United States Patent
Schreiber

Patent Number: 5,254,119
Date of Patent: * Oct. 19, 1993

[54] OSTEOTOMY DEVICE AND METHOD THEREFOR

[76] Inventor: Saul N. Schreiber, 6525 N. Central Ave., Phoenix, Ariz. 85012

[ * ] Notice: The portion of the term of this patent subsequent to Jan. 7, 2009 has been disclaimed.

[21] Appl. No.: 749,426

[22] Filed: Aug. 23, 1991

[51] Int. Cl.⁵ .................. A61F 5/00; A61F 2/32
[52] U.S. Cl. ........................... 606/87; 606/96
[58] Field of Search ............... 606/86, 87, 88, 96, 606/97, 98, 102, 104, 105, 79

[56] References Cited

U.S. PATENT DOCUMENTS

| | | | |
|---|---|---|---|
| 4,335,715 | 6/1982 | Kirkley | 606/87 |
| 4,349,018 | 9/1982 | Chambers | 606/88 |
| 4,421,112 | 12/1983 | Mains | 606/88 |
| 4,565,191 | 1/1986 | Slocum | 606/87 |
| 4,567,885 | 2/1986 | Androphy | 606/88 |
| 4,627,425 | 12/1986 | Reese | 606/87 |
| 4,632,102 | 12/1986 | Comparetto | 606/87 |
| 4,703,751 | 11/1987 | Pohl | 606/87 |
| 4,738,253 | 4/1988 | Buechel | 606/96 |
| 4,759,350 | 7/1988 | Dunn | 606/82 |
| 5,049,149 | 9/1991 | Schmidt | 606/87 |

Primary Examiner—Michael Brown
Attorney, Agent, or Firm—Harry M. Weiss

[57] ABSTRACT

This invention relates to a device and method therefor used in osteotomy for removing a right-angled bone wedge from a leg bone. The device consists of a trapezoidal block having one column of transverse bores and other columns of oblique bores. The columns of oblique bores are positioned at predetermined angles from the column of transverse bores. A first tower member is mounted atop the block. The first tower also has a plurality of transverse bores that align with the transverse bores in the block. A surgical pin can be inserted through the tower until the tip of this pin lies above the apex of the bone wedge to be cut. Surgical pins are then inserted through the corresponding transverse bores in the block and drilled into the bone until the ends of these pins align with the end of the first pin inserted in the first tower. This procedure establishes the height of the bone wedge. A second tower is coupled to an oblique bore at the desired predetermined angle. The second tower also has a plurality of transverse bores. A surgical pin is inserted through one of the bores in the second tower until the tip of this pin abuts the tip of the pin inserted in the first tower. Surgical pins are then inserted through the corresponding oblique bores in the block and drilled in the bone until the ends of these pins are aligned with the end of the first pin inserted in the second tower.

4 Claims, 4 Drawing Sheets

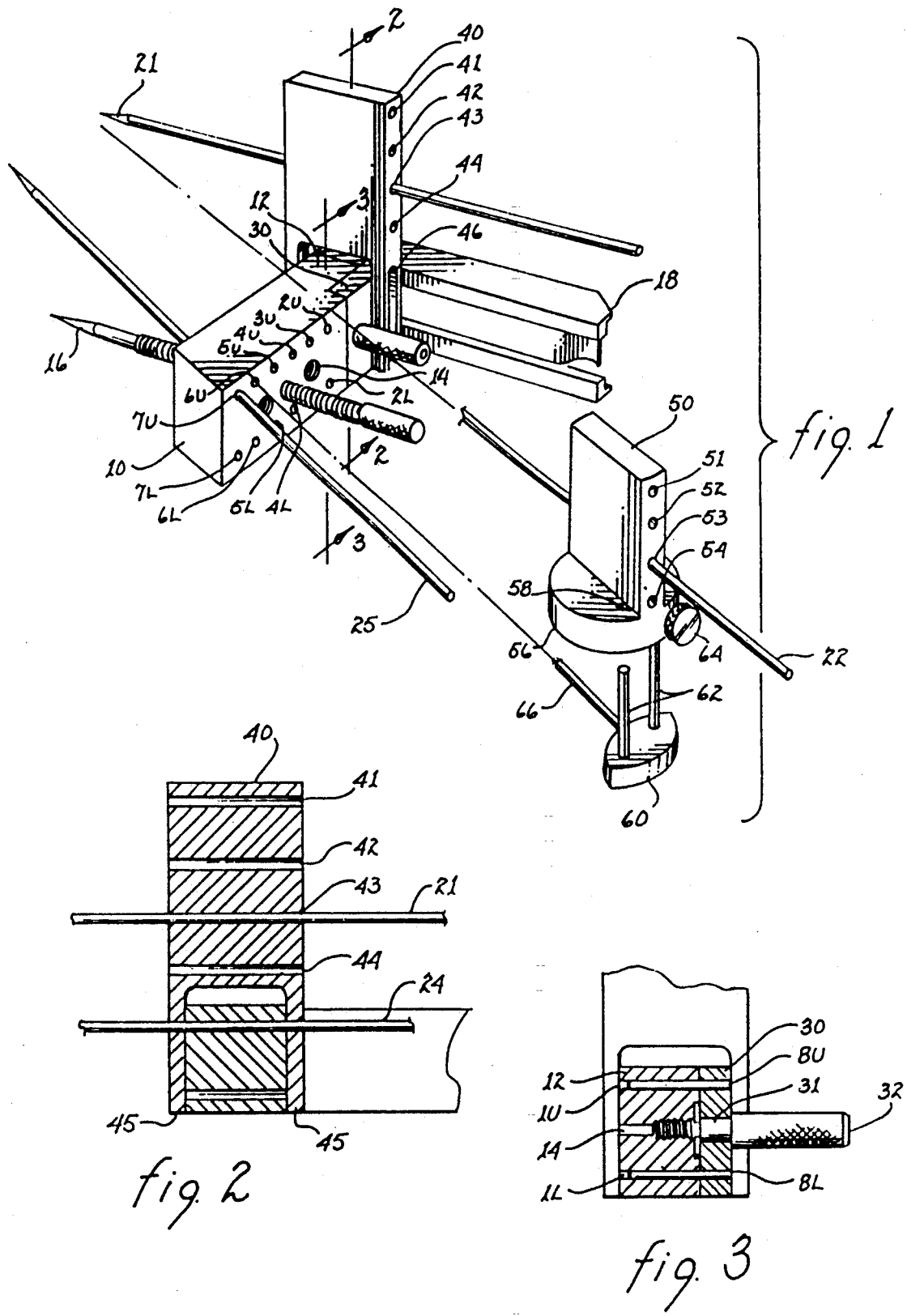

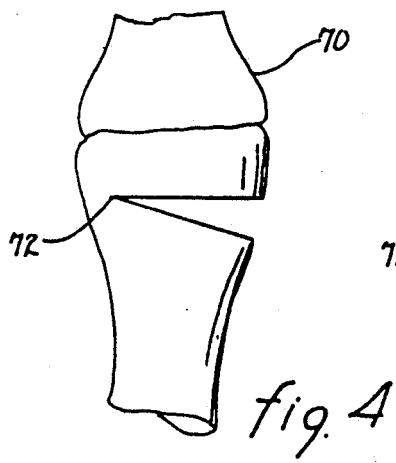
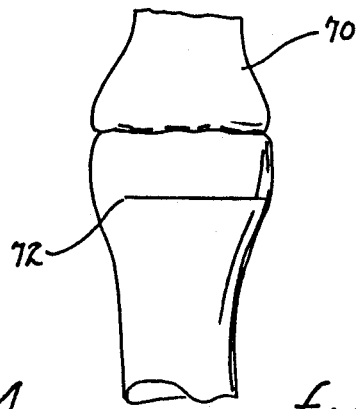
fig. 4  fig. 5
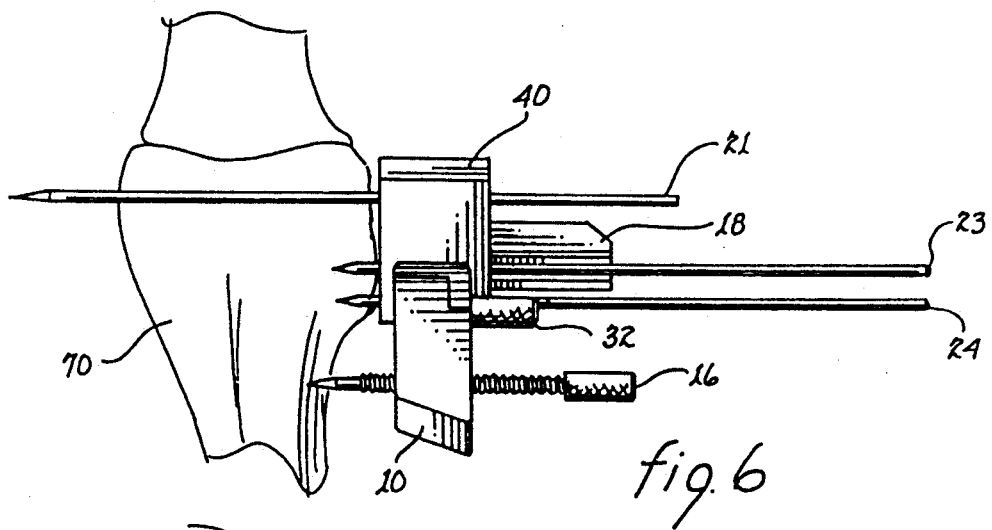
fig. 6
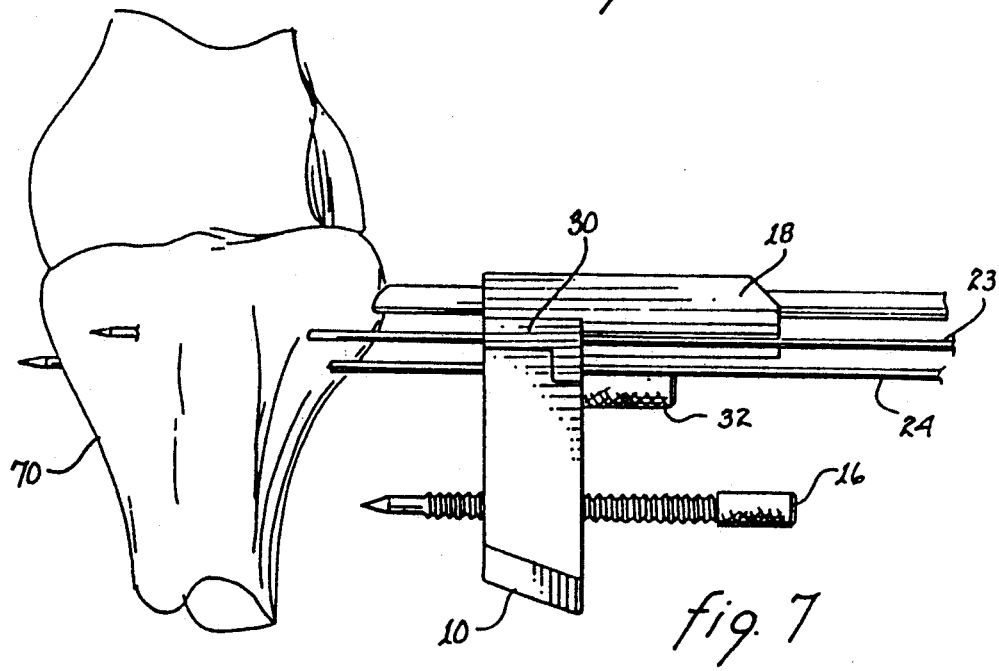
fig. 7

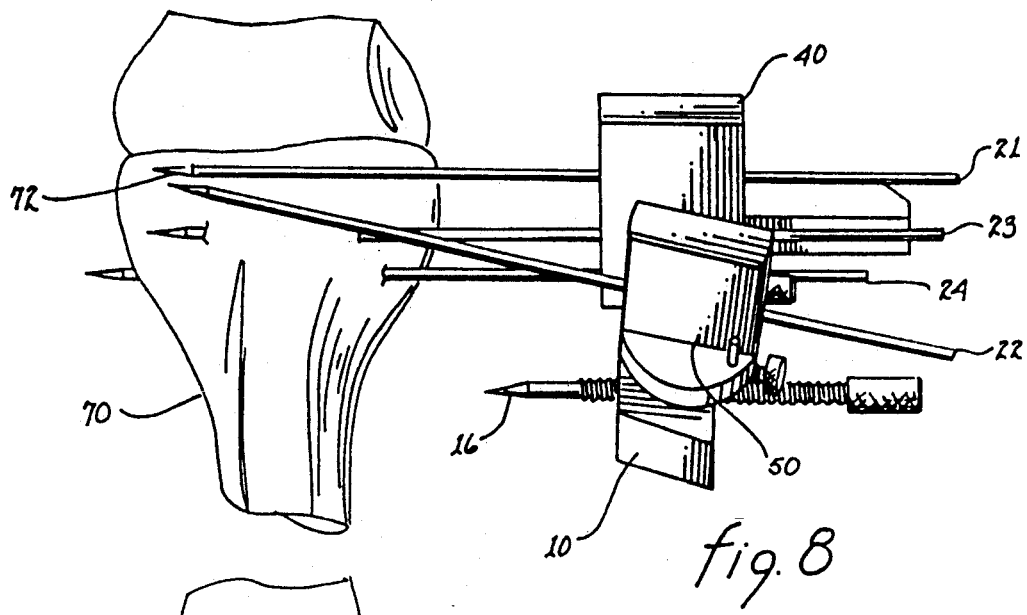
fig. 8
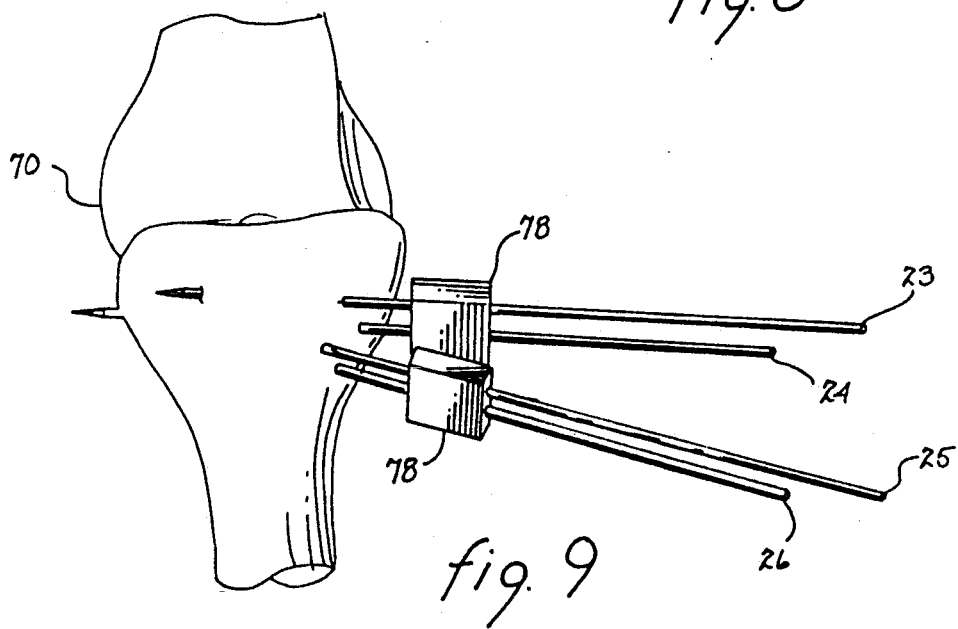
fig. 9
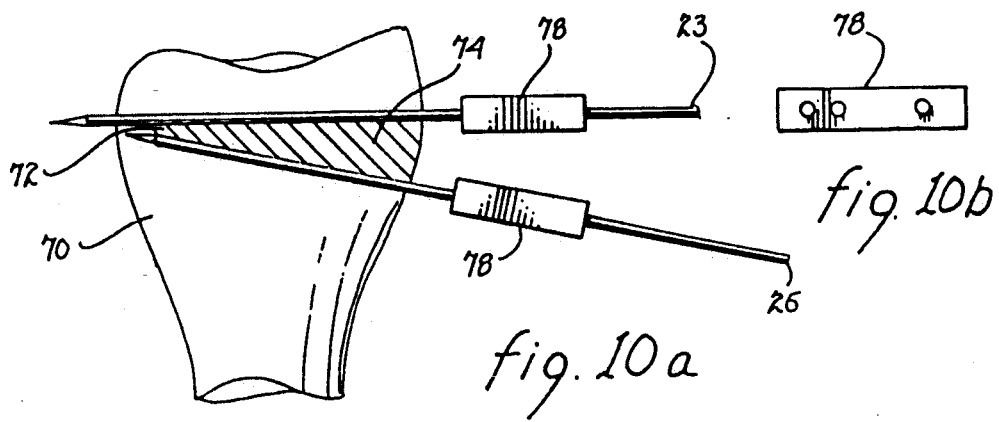
fig. 10a
fig. 10b

OSTEOTOMY DEVICE AND METHOD THEREFOR

FIELD OF INVENTION

This invention relates generally to an osteotomy device and method therefor and more particularly, to an osteotomy device and method therefor for precisely locating two intersecting bone cuts below a person's knee portion so that a bone wedge can be removed to correct for leg deformities such as for bowleggedness.

BACKGROUND OF THE INVENTION

Osteotomy is a surgical procedure which involves cutting and removing a section of bone. The procedure is used to correct many types of bone deformities found in the human leg. For example, in the instance of improper leg formation during growth, undesired angulation or orientation of a particular bone with respect to other bones of the leg often occurs such as the condition referred to as bowleggedness the surgical procedure for overcoming this type of medical problem normally involves the removal of a wedge-shaped section of the knee portion of the malformed or misaligned leg at a predetermined location which causes the relative repositioning of the remaining bone sections of the leg so as to impart to the surgically corrected leg the proper relative configuration or orientation. The wedge-shaped section removed from the original knee bone is, of course, of a predetermined size which naturally depends upon extent of the correction required. For example, by known techniques, an orthopedic surgeon can determine the extent of leg deformity and the required amount of a wedge that is needed to correct the leg deformity.

To make the correct adjustment to the leg requires not only cutting out the correctly sized bone wedge portion at a proper angle, but also assuring that there remains, at the apex of the wedge, residual bone of sufficient thickness to prevent a complete severance or fracture of the bone and to promote mending together of the cut or bone portions. Also, to ensure correct realignment of the bone, it is essential that the cuts into the bone, performed to remove the wedge-shaped segment, be substantially smooth and planar so that, when the severed end regions of portions of the remaining bone segments are brought into contact their surfaces mate uniformly across the entire severed surfaces to promote rapid and structurally effective mending of the cut bone portion. Furthermore, to assure this rapid mending, often times a suitably shaped blade plate or side plate is coupled, by screws, to the remaining bone segments, after removal of the wedge portion, and is used to hold the segments together. To properly use such a blade plate this requires that the removed wedge portion have a right angle configuration.

U.S. Pat. No. 4,335,715 issued Jun. 22, 1982 to W. H. Kirkley or "Osteotomy Guide" discloses an apparatus in which a pair of pins positioned on an arcuate track are inserted into the bone to serve as a guide for the surgeon in making cuts into the bone. The device has no means for determining the apex of the wedge. Therefore, the surgeon must rely on his judgment to determine the apex or remove an entire wedge without leaving any residual bone. Obviously, such a procedure complicates the healing process.

U.S. Pat. No. 4,349,018, issued Sept. 14, 1982 to G. R. Chambers for "Osteotomy Apparatus" discloses a fairly complex and cumbersome device for guiding saw cuts in a operation for the total removal of the Knee. Because of the device's complexity it is ill suited for simpler osteotomy procedures.

U.S. Pat. No. 4,627,425, issued Dec. 9, 1986 to H. W. Reese for "Osteotomy Appliances and Method" discloses a guide to be used by the surgeon to make a second cut in a bone at a predetermined angle from a first cut. To locate the apex of the wedge, a pin has to be inserted vertically into the bone. Also, the device produces a wedge without a right angle and therefore cannot be used with the blade plate or side plate described above.

U.S. Pat. No. 4,757,810, issued Jul. 19, 1988 to H. W. Reese for "Osteotomy Apparatus and Method" discloses a guide for precisely locating two parallel, spaced apart bone cuts. This guide however cannot be used to cut a wedge from the bone.

Still there is a need for a osteotomy guide that would allow a surgeon to remove a pre-calculated sized bone wedge having a right angle, that would leave a sufficient amount of residual bone and that does not require drilling a vertical pin into the bone to locate the apex of the wedge.

SUMMARY OF THE INVENTION

An object of the present invention is to provide an osteotomy device and method therefor for removing a bone wedge having a right angle.

Another object of the present invention is to provide an osteotomy device and method therefor that can locate the apex of a bone wedge to be removed without drilling a pin vertically into the bone.

Yet another object of the present invention is to provide an osteotomy guide and method therefor that would enable the surgeon to leave a sufficient amount of residual bone after making the cuts into the bone (for example of a wedge of bone) so as to inhibit the fracturing of the bone.

The subject invention accomplishes these objects by providing a device and method therefor that allows the surgeon to establish a reference external to the bone as to the position of the apex and angle of the wedge to be cut and then translate those references into the bone thus establishing precise bone channels that are to be cut.

These and other objects, features and advantages of the present invention, as well as details of the preferred embodiment thereof, will be more fully understood from the following description and drawing.

BRIEF DESCRIPTION OF THE DRAWING

FIG. 1 is a perspective view of the osteotomy device of this invention.

FIG. 2 is a cross-sectional view taken along line 2—2 of FIG. 1.

FIG. 3 is a cross-sectional view taken along line 3—3 of FIG. 1.

FIG. 4 is a vertical side view of a model of a leg bone with a bone wedge removed before straightening out the bottom let portion.

FIG. 5 is a vertical side view of the same leg model reoriented after the bone wedge has been removed showing the bottom leg portion straightened out with respect to the knee portion.

FIG. 6 is a perspective view of the osteotomy device positioned next to the model of the leg bone after insertion of a first (top pin) therein.

FIG. 7 is a perspective view with the top tower of the ostectomy device of FIG. 6 removed and the lower transverse pins drilled into the bone model.

FIG. 8 is a perspective view of the osteotomy device of FIGS. 6 and 7 with an external oblique pin aligned at a predefined angle with the transverse pin.

FIG. 9 shows the lower oblique and transverse pins forming the shape of the wedge to be removed from the model of the leg bone after the procedure of FIG. 8.

FIG. 10a is a view similar to FIG. 9 with a portion representing the bone wedge to be removed shown in cross-sectional.

FIG. 10b is a side-elevational view of the block used with the pins of the osteotomy device.

DESCRIPTION OF THE PREFERRED EMBODIMENT

Figure 11:
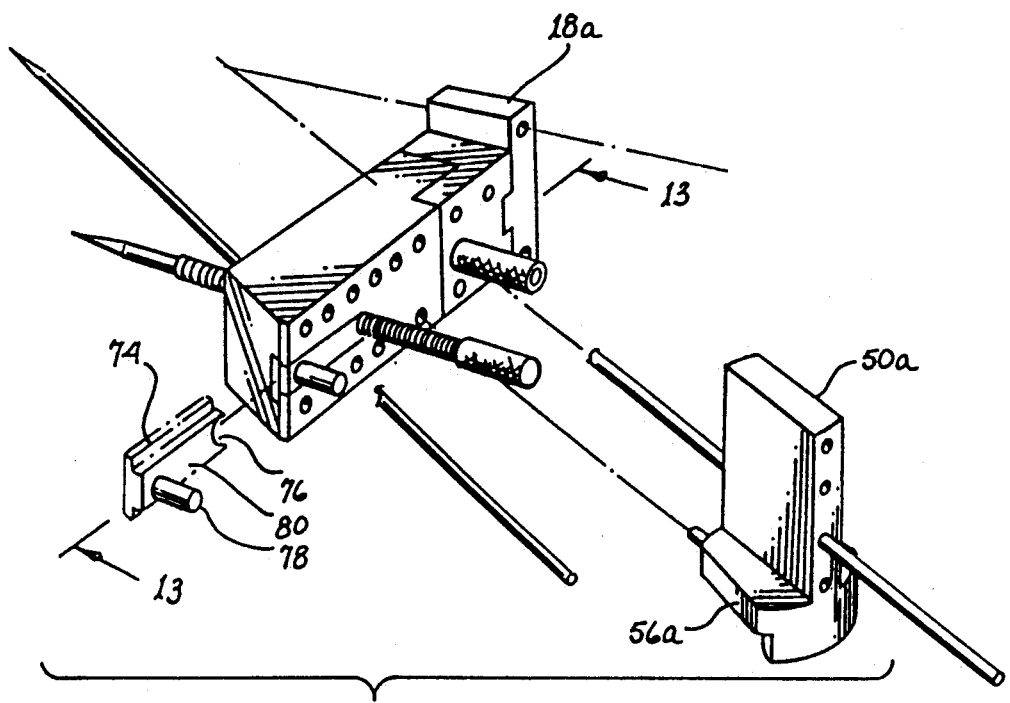
FIG. 11 is an exploded, perspective view of an alternative embodiment of the osteotomy device in accordance with this invention.
Figure 13:
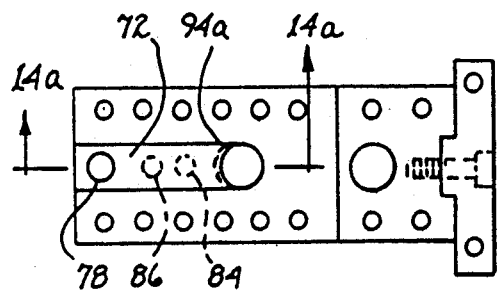
FIG. 13 is a cross-sectional view taken along line 13—13 of FIG. 11.
Figure 12:
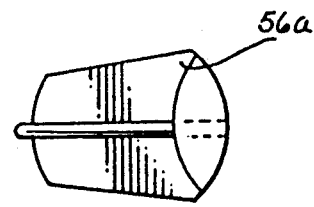
FIG. 12 is a bottom view of the second rectangular tower of the alternative embodiment of FIG. 11.
Figure 14A:
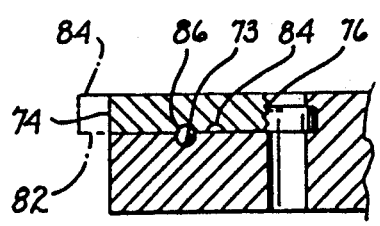
FIG. 14a is a cross-sectional view taken along line 14a—14a of FIG. 13 showing the positioning pin engaged.
Figure 14B:
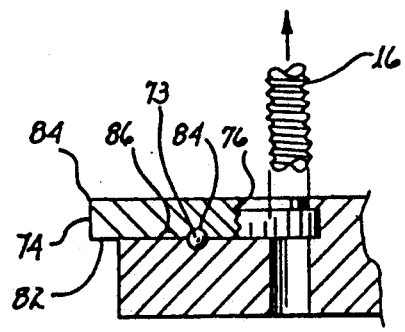
FIG. 14b is a cross-sectional view taken along line 14a—14a of FIG. 13 showing the positioning pin disengaged.

In the preferred embodiment (see FIG. 1) the subject invention comprises a substantially trapezoidal shaped block 10. The distal end 12 of the block 10 is recessed to receive a L-shaped connecting member 30. The distal end 12 has two transverse bores 1U and 1L extending therethrough. The two bores 1U and 1L lie in the same vertical plane, which is perpendicular to the length of the block 10. The subscript U indicates the upper bore and the subscript L indicates the lower bore. The distal end 12 also has a threaded hole 14 for receiving a connecting pin 32. Disposed in the same horizontal plane as the bore 1U is a transmittal means that includes a plurality of oblique bores, 2U,3U,4U,5U,6U and 7U and disposed in the same horizontal plane as the bore 1L a plurality of oblique bores, 2L,3L,(now shown) 4L, 5L,6L and 7L. Bores having the same numerical subscript reside in the same vertical plane. The bores 2U,2L are angled 7½ degrees from the vertical plane passing through the bores 1U,1L. Each succeeding set of bores is displaced an additional 2½ degrees from the preceding set of bores. For example, the bores 3U,3L are angled 2½ degrees from the bores 2U,2L and 9½ degrees from the bores 1U,1L. Each of these bores has the same diameter which is selected to tightly receive one of the surgical pins 20. Disposed between the upper row of the bores 2U-7U and the lower row of the bores 2L-7L are three threaded holes 14 which extend through the block 10, perpendicular to the length of the block 10. The holes 14 are sized to receive a positioning pin 16. The positioning pin 16 has a pointed end, a threaded middle section and a grip on the other end to facilitate the insertion and removal of the positioning pin 16.

The L-shaped connecting member 30, (see FIG. 3), has a threaded hole 31 for receiving the connecting pin 32 and two transverse bores 8U,8L. The connecting member 30 is sized and shaped so that when it is attached to the distal end 12 of the block 10 by inserting the connecting pin 32 through hole 31 and hole 14, the bores 8U,8L align with the bores 1U,1L respectfully. A guide 18, for a bone chisel or drill, is attached to the connecting member 30 so that the guide 18 is perpendicular to the block 10. This two part design combining the connecting member 30 to the distal end 12 by the connecting pin 32 allows for fast and easy removal of the guide 18 from the block 10 after the surgical pins 20 have been inserted into the bone without disturbing the position of the inserted surgical pins 20.

An external locator means includes a first rectangular tower 40, (see FIG. 2), has four transverse bores 41,42,43 and 44 extending therethrough. Each of the bores 41,42,43 and 44 are sized to receive one of the surgical pins 21-26 and lie in the same vertical plane but at different heights. Extending downward from the bottom of the tower 40 are two legs 45. The distance between the two legs 45 is selected to allow the two legs 45 to slip fit over the distal end 12 and connecting member 30 after the connecting member 30 has been attached to the block 10. Each of the legs 45 has a slit 46 to assure that the legs 45 do not block bores 1U,1L,8U and 8L.

The external locator means also includes a second rectangular tower 50, (see FIG. 1), has four transverse bores 51,52,53 and 54 extending therethrough. Each of the bores 51,52,53 and 54 are sized to receive one of the surgical pins 20 and lie in the same vertical plane but at different heights. The tower 50 has an ovate base 56 with two vertical holes 58. The two holes 58 are sized to receive two prongs 62 extending upward from an ovate member 60 positioned below the base 56. The height of the tower 50 can be adjusted by sliding the base 56 up and down the two prongs 62. The two prongs 62 can be locked into the base 56 by tightening a locking pin 64. Extending horizontally from the ovate member 60 is a prong 66 which is sized to be inserted into any of the bores 2U-7U and 2L-7L.

An internal locator means includes surgical pins 21-26, which are all of identical length. Each of the pins 22-26 has a pointed end and is strong enough to be drilled into bone without bending. Six surgical pins 21-26 are required when using the subject invention. For illustrative purposes only the surgical pins 20 are identified in the drawings and in the following description as follows. Surgical pin 21 is inserted through the bore 43 in the tower 40. Surgical pin 22 is inserted through the bore 53 in the tower 50. Surgical pin 23 is inserted through the bores 1U and 8U. Surgical pin 24 is inserted through the bores 1L and 8L. Surgical pin 25 is inserted through the bore 7U Surgical pin 26 is inserted through the bore 7L.

Each of the components of the subject invention is preferably made of metal and can be sterilized.

In the preferred embodiment, (see FIG. 4-10), the subject invention would operate as follows. Starting from the point where all of the components are disassembled. First, the distal end 12 of the block 10 is coupled to the connecting member 30 by inserting the connecting pin 32 through the holes 14 and 31. The guide 18 is then attached to the connecting member 30. This combination of components is positioned adjacent to the subject bone 70 which is illustrated in skeletal form in the drawings. The positioning pin 16 is inserted through one of the holes 14 until the tip of the pin 16 abuts the bone 70. This assures that the block 10 is parallel to the bone 70. The tower 40 is then slip fit over the distal end 12 and connecting member 30 so that the bores 41-44 lie in the same vertical plane as the bores 1U,1L,8U 8L. The surgical pin 21 is inserted through the bore 43. The selection of the bore 43 is for illustrative purposes only. In actual operation the choice of which bore to use is determined by the thickness of the soft tissue of the leg. The bore that allows the surgical pin 21 to pass closest to the leg without touching the leg is preferably selected. The surgical pin 21 is inserted through the bore 43 until the surgeon estimates that the tip of the pin 21 is directly above the apex 72 of the bone wedge 74. The position of the pin 21 relative to the apex 72 is then checked by X-rays and any adjustments are made as needed to the position of the pin 21. The surgeon then slides the surgical pin 23 through the bores 1U,8U and surgical pin 24 through the bores 1L,8L. These pins 23 and 24 are then drilled into the leg until the ends of pins 23 and 24 align with the end of the pin 21. Once this procedure is completed the position of the apex 72 of the bone wedge 74 is established. Also, should the device be accidently moved it can always be accurately realigned by sliding the device along the pins 23 and 24 until the ends of the pins 23,24 and 21 are once again aligned.

As one skilled in the art would know, the angle of the bone wedge is substantially equal to the angle through which the leg must be rotated to realign the lower leg. Assuming this angle is twenty degrees, the surgeon then inserts the prong 66 through the bore 7U. The height of the tower 50 is adjusted until the bore 53 lies at the same height as the bore 43. The locking pin 64 is tightened securing the position of the tower 50. The surgical pin 22 is inserted through the bore 53 until the tip of the pin 22 meets the tip of the pin 21. If these two tips do not meet, the position of pin 21 is adjusted as described above which will result in the two tips meeting. The surgical pin 26 is inserted through the bore 7L and drilled into the bone 70 until the end of the pin 26 aligns with the end of the pin 22. The tower 50 along with the pin 22 is then removed and the surgical pin 25 is inserted through the bore 7U and drilled into the bone 70 until the end of the pin 25 aligns with the end of the pin 26. The tower 40 along with the pin 21 is removed. The connecting pin 32 is unscrewed and the connecting member 30 along with the guide 18 is removed by sliding the connecting backward over the pins 23 and 24. The block 10 is then removed by sliding it backwards over the pins 23,24,25 and 26. A cutting block 78 is slid over each of the remaining pair of pins to establish a channel in which to cut the bone.

FIGS. 11-14b show an alternative embodiment of the subject osteotomy device. The differences between the this alternative embodiment and the preceding embodiment are as follows.

The guide 18 is replaced by a side plate 18a for inserting screws (not shown) into the leg. Both the guide 18 and the side plate 18a are standard equipment used in osteotomy procedures. The base 56a of the second rectangular tower 50a is now integral with the tower 50a. The holes 58, the prongs 62 and the locking pin 64 of the original embodiment have been removed. The three holes 14 in block 10 have been reduced to a single, unthreaded hole 94a (see FIG. 13) in the block 10a. The block 10a has a channel 72 (see FIG. 13) for receiving a locking member 74 (see FIG. 11). The channel 72 has a spring loaded divot 73 (see FIGS. 14a and 14b). The locking member 74 has a threaded end 76 (see FIGS. 11, 14a and 14b), a gripping member 78 (see FIGS. 11 and 13) disposed on its front side 80 (see FIG. 11) and on its backside 82 (see FIGS. 14a and 14b) are two positioning slots 84, and 86 which engage the divot 73 as the locking member 74 is moved. The locking member 74 has three positions. At the first position, (see FIG. 14a), the divot 73 engages the slot 86 and the threaded end 76 engages the threaded middle section of the positioning pin 16. In this configuration, the positioning pin 16 can only be moved by screwing or unscrewing the positioning pin 16 along its threaded middle section. By pushing on the gripping member 78, the divot 73 is dislodged from the slot 86 and the locking member 74 can be moved to the second position, (see FIG. 14b), where the divot 73 engages the slot 84. At this position, the positioning pin is free to be slid in and out and can easily be removed without upsetting the position of the osteotomy device of the subject invention. Lastly, as shown in FIG. 11 the locking member 74 can be entirely removed from the block 10a.

The osteotomy devices described in the preferred and alternate embodiments can be rotated so that they can be used on both left and right legs.

While the invention has been particularly shown and described with reference to a preferred embodiment thereof, it will be understood by those skilled in the art that changes in form and detail may be made therein without departing form the spirit and the scope of the invention.

I claim:

1. An osteotomy guide used in the removal of a wedge shaped piece of bone from a patient's leg, said piece of bone having first and second sides that intersect at the apex of the wedge, the angle between said first and second sides being substantially equal to the angle through which said leg must be rotated to correct the leg's misalignment, which comprises:

block means for establishing a reference alignment with respect to said patient's leg;

external locator means coupled to said block means for locating the positions of said apex and said first and second sides of said bone wedge externally above said patient's leg;

internal locator means coupled to said block means for transferring said positions of the apex and said first and second sides of said bone wedge form said external locator means to corresponding locations inside said bone of said patient's leg;

said block means comprises positioning pin means coupled to said block means for positioning said block means parallel to said bone of said patient's leg to establish said reference alignment, said block means further comprises transmittal means for transmitting said positions determined by said external locator means to said internal locator means, said external locator means disposed atop said transmittal means, said internal locator means being integral with said transmittal means; and further comprising a plurality of surgical pins;

said transmittal means further comprises a first column of transverse bores extending therethrough and a plurality of columns of oblique bores extending therethrough, said oblique bores being aligned with said transverse bores and said columns of oblique bores positioned at predetermined angles from said first column of transverse bores, said transverse and oblique bores being sized to receive said surgical pins, and said columns of transverse bores and oblique bores are aligned so as to form an upper row of bores and a lower row of bores.

2. The device recited in claim 1 further comprising a guide means coupled to said block means for aligning a bone cutting device with said corresponding locations inside said bone of said patient's leg.

3. The device recited in claim 1 wherein said external locator means further comprises:

a first tower member having a plurality of transverse bores sized to receive a number of surgical pins for extending therethrough; and a second tower member having a plurality of transverse bores sized to receive a number of said surgical pins for extending therethrough coupled to one of said oblique bores so that said transverse bores of said second tower are aligned at the same predetermined angle as said oblique bores coupled thereto.

4. The device recited in claim 1 wherein said internal locator means is further comprised of said surgical pins inserted through said transverse and oblique bores of said lower row.

* * * * *